US007288637B2

(12) United States Patent
Solomon et al.

(10) Patent No.: US 7,288,637 B2
(45) Date of Patent: Oct. 30, 2007

(54) SINGLE CHAIN ANTIBODY AGAINST MUTANT P53

(75) Inventors: Beka Solomon, Herzlia Pituach (IL); Gerald Cohen, Raanana (IL); Dimitri Govorko, Herzlia (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 875 days.

(21) Appl. No.: 10/247,488

(22) Filed: Sep. 20, 2002

(65) Prior Publication Data

US 2003/0022244 A1    Jan. 30, 2003

Related U.S. Application Data

(63) Continuation of application No. 09/526,738, filed on Mar. 16, 2000, now Pat. No. 6,630,584.

(51) Int. Cl.
*C07K 16/00* (2006.01)
(52) U.S. Cl. .............................. 530/387.7; 530/387.1; 530/387.3; 530/387.9; 530/388.8; 530/388.85
(58) Field of Classification Search ............. 424/130.1, 424/133.1, 135.1, 137.1, 138.1, 141.1, 142.1, 424/143.1, 152.1, 155.1, 139.1, 156.1; 514/44; 530/388.8, 388.85, 387.7, 387.1, 387.3, 387.9; 536/24.5
See application file for complete search history.

(56) References Cited

U.S. PATENT DOCUMENTS

| 4,816,567 | A | * | 3/1989 | Cabilly et al. ............ 530/387.3 |
| 5,091,513 | A | | 2/1992 | Huston et al. |
| 5,258,498 | A | * | 11/1993 | Huston et al. ............... 530/350 |
| 5,618,920 | A | * | 4/1997 | Robinson et al. ........ 530/387.1 |
| 5,756,669 | A | * | 5/1998 | Bischoff et al. ............ 530/350 |
| 6,630,584 | B1 | | 10/2003 | Solomon et al. |
| 2002/0155114 | A1 | * | 10/2002 | Marks et al. ............ 424/150.1 |

OTHER PUBLICATIONS

Rudikoff et al (Proc. Natl. Acad. Sci. USA 1982 vol. 79 p. 1979).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987).*
Lin et al Biochemistry USA vol. 14:1559-1563 (1975).*
Acland et al., Nature vol. 343:662-665 (1990).*
Ibragimova and Eade (Biophysical Journal, Oct. 1999, vol. 77, pp. 2191-2198).*
Orlandi et al (Proc. Natl. Acad. Sci. USA, 86:3833-3837, 1989).*
Marasco, W.A., "Intracellular antibodies (intrabodies) as research reagents and therapeutic molecules for gene therapy", *Immunotechnology*, vol. 1, pp. 1-19, (1995).
Jannot, C.B., et al., "Characterization of scFv-421, a Single-Chain Antibody Targeted to p53", *Biochemical and Biophysical Research Comm.*, vol. 230, No. 2, pp. 242-246, (1997).
Yewdell, J.W., et al., "Monoclonal Antibody Analysis of p53 Expression in Normal and Transformed Cells", *Journal of Virology*, vol. 59, No. 2, pp. 444-452, (Aug. 1986).
Harlow, E., et al., "Monoclonal Antibodies Specific for Simian Virus 40 Tumor Antigens", *Journal of Virology*, Vo. 39, No. 3, pp. 861-869, (Sep. 1981).
Gannon, J.V., et al., "Activating mutations in p53 produce a common conformational effect. A monoclonal antibody specific for the mutant form", *The EMBO Journal*, vol. 9, No. 5, pp. 1595-1602, (1990).
Gamble, J., et al., "Evidence that Immunological Variants of p53 Represent Alternative Protein Conformations", *Virology*, vol. 162, pp. 452-458, (1988).
Stephen, C.W., et al., "Mutant Conformation of p53 Precise Epitope Mapping Using a Filamentous Phage Epitope Library", *J. Mol. Biol.* vol. 225, pp. 577-583, (1992).
Cohen, P.A., et al., "Characterization of a new intrabody directed against the N-terminal region of human p53", *Oncogene*, vol. 17, pp. 2445-2456, (1998).
Milner, J., et al., "A new anti-p53 monoclonal antibody, previously reported to be directed against the large T antigen of simian virus 40", *Oncogene*, vol. 1, pp. 453-455, (1987).
Bowie et al., Science, vol. 247, pp. 1306-1310, 1990.
Burgess et al., Journal of Cell Biology, vol. 111, pp. 2129-2138, 1990.
Lazar et al., Molecular and Cell Biology, vol. 8, pp. 1247-1252, 1988.
Bork, Genome Research, vol. 10, pp. 398-400, 2000.
Jones et al., Advanced Drug Delivery Reviews, vol. 31, pp. 153-170, 1998.
Anderson, Nature, vol. 392, pp. 25-30, 1998.
Verma et al., Nature, vol. 389, pp. 239-242, 1997.
Ross et al., Human Gene Therapy, vol. 7, pp. 1781-1790, 1996.
Cohen et al., Science, vol. 265, pp. 1371-1371, 1994.
Cohen et al. "Characterization of A New Intrabody Directed Against the N-Terminal Region of Human P53", Oncogene, 17(19): 2445-2456, 1998. Abstract, p. 2452, col. 1; Claims: 1-29.
Caron de Fromentel et al. "Restoration of Transcriptional Activity of P53 Mutants in Human Tumour Cells by Intracellular Expression of Anti-P53 Single Chain Fv Fragments", Oncogene, 18(2): 551-557, 1999. Abstract, p. 556, Fig.6; Claims: 1-29.
Jannot et al. "Characterization of SCFV-421, A Single-Chain Antibody Targeted to P53", Biochemical and Biophysical Research Communications, 230(2): 242-246, 1997. Abstract, p. 245, col. 1-2; Claims: 1-29.

(Continued)

*Primary Examiner*—David J. Blanchard
*Assistant Examiner*—Parithosh K. Tungaturthi

(57) ABSTRACT

More than 90% of mutations found in the p53 protein produce a conformational change in p53 which results in the exposure of an epitope, which is otherwise hidden in the hydrophobic core of the molecule. A single chain antibody (scFv) which specifically recognizes this common mutant epitope in mutant p53 but not in wild type p53 is disclosed. Also described are a DNA molecule encoding the scFv, pharmaceutical compositions comprising the antibody and methods of treatment using the pharmaceutical compositions.

2 Claims, 7 Drawing Sheets

OTHER PUBLICATIONS

Figure 1A:
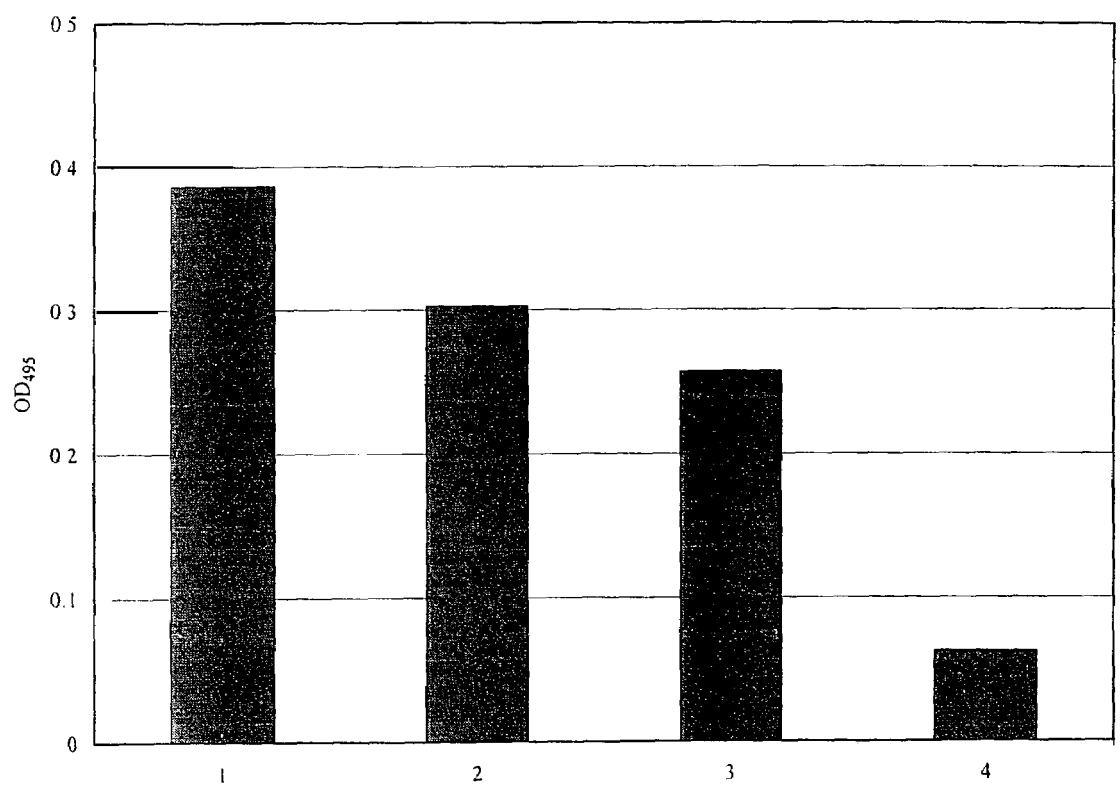

Govorko et al. "Single-Chain Antibody Against the Common Epitope of Mutant P53: Isolation and Intracytosolic Expression in Mammalian Cells", Journal of Immunological Methods, 258(1-2): 169-181, 2001. Abstract. p. 179, col. 2; Claims: 1-29.

Fischer-Fantuzzi et al. "Cell-Dependent Efficiency of Reiterated Nuclear Signals in A Mutant Simian Virus 40 Oncoprotein Targeted to the Nucleus", Mol. Cell Biol., 8(12): 5495-5503, 1988. Abstract.

Pavlinkova et al. "Effects of Humanization and Gene Shuffling on Immunogenicity and Antigen Binding of Anti-TAG-72 Single-Chain Fvs", Int. J. Cancer, 94(5): 717-726, 2001. Abstract.

Cheson "Rituximab: Clinical Development and Future Directions", Expert. Opin. Biol. Ther., 2(1): 97-110, 2002. Abstract.

Grillo-Lopez et al. "Monoclonal Antibodies: A New Era in the Treatment of Non-Hodgkin's Lymphoma", Curr. Pharm. Biotechnol., 2(4): 301-311, 2001. Abstract.

Kashmiri et al. "Development of A Minimally Immunogenic Variant of Humanized Anti-Carcinoma Monoclonal Antibody CC49", Crit. Rev. Oncol. Hematol., 38(1): 3-16, 2001. Abstract.

Keating et al. "Emerging Information on the Use of Rituximab in Chronic Lymphocytic Leukemia", Semin. Oncol., 29(1 Suppl.2): 70-74, 2002. Abstract.

Hortobagyi "Overview of Treatment Results With Trastuzumab (Herceptin) in Metastatic Breast Cancer", Semin. Oncol., 28(6 Suppl.18): 43-47, 2001. Abstract).

Munro et al. "A C-Terminal Signal Prevents Sectetion of Luminal ER Proteins", Cell, 48(5): 899-907, 1987. Abstract.

Silver "How Proteins Enter the Nucleus", Cell, 64(3): 489-497, 1991. Abstract.

Wu et al. "Humanization of A Murine Monoclonal Antibody by Simultaneous Optimization of Framework and CDR Residues", J. Mol. Biol., 294(1): 151-162, 1999. Abstract.

Barbas et al. "Selection and Evolution of High-Affinity Human Anti-Viral Antibodies", TIBTECH, 14: 230-234, 1996.

Brown et al. "Tolerance to Single, But Not Multiple, Amino Acid Replacements in Antibody VH CDR2. A Means of Minimizing B Cells Wastage From Somatic Hypermutation?", The Journal of Immunology, 156: 3285-3291, 1996. Abstract.

Nishimiya et al. "Thermodynamic Consequences of Grafting Enhanced Affinity Toward the Mutated Antigen Onto An Antibody. The Case of Anti-Lysozyme Antibody, HyHEL-10", The Journal of Biological Chemistry, 275(17): 12813-12820, 2000.

Gamble et al. "Evidence That Immunological Variants of P53 Represent Alternative Protein Conformations", Virology, 162(2): 452-458, 1988. Abstract.

Gannon et al. "Activating Mutations in P53 Produce A Common Conformational Effect. A Monoclonal Antibody Specific for the Mutant Form", The EMBO Journal, 9(5): 1595-1602, 1990.

Harlow et al. "Monoclonal Antibodies Specific for Simian Virus 40 Tumor Antigens", Journal of Virology, 39(3): 861-869, 1981.

Marasco "Intracellular Antibodies (Intrabodies) as Research Reagents and Therapeutic Moleculaes for Gene Therapy", Immunotherapy, 1: 1-19, 1995.

Milner et al. "A New Anti-P53 Monoclonal Antibody, Previously Reported to Be Directed Against the Large T Antigen of Simian Virus 40", Oncogene, 1(4): 453-455, 1987.

Murray et al. "Codon Usage in Plant Genes", Nucleic Acids Research, 17(2): 477-498, 1989.

Smythe et al. "Production of Linear Polymers of HIV Gp120-Binding Domains", Protein Engineering, 7(2): 145-147, 1994. Abstract.

Stephen et al. "Mutant Confimation of P53 *1. Precise Epitope Mapping Using A Filamentous Phage Epitope Library", Journal of Molecular Biology, 225(3): 577-583, 1992. Abstract.

Yewdell et al. "Monoclonal Antibody Analysis of P53 Expression in Normal and Transformed Cells", Journal of Virology, 59(2): 444-452, 1986.

Verma et al. "Gene Therapy—Promises, Problems and Prospects", Nature, 389: 239-242, 1997.

Bowie et al. "Deciphering the Message in Protein Sequence: Tolerance to Amino Acid Substitutions", Science, 247(4948): 1306-1310, 1990.

Bork "Powers and Pitfalls in Sequence Analysis: The 70% Hurdle", Genome Research, 10: 398-400, 2000.

Marasco et al. "Antibodies for Targeted Gene Therapy: Extracellular Gene Targeting and Intracellular Expression", Advanced Drug Delivery Reviews, 31(1-2): 153-170, 1998. Abstract.

* cited by examiner

```
  1      CAGG TCAAACTGCA GCAGTCTGGG GCTGAACTGG CAAAACCTGG GGCCTCAGTG
            Q   V  K  L   Q  Q  S  G   A  E  L   A  K  P   G  A  S  V

61      AAGATGTCCT GCAAGACTTC TGGCTACACC TTTACTAGCT ACTGGATGAA CTGGGTAAAA
          K  M  S   C  K  T   S  G  Y  T   F  T  S   Y  W  M   N  W  V  K

121      CAGAGGCCTG GACAGGGTCT GGAATGGATT GGATACATTA ATCCTACCAC TGGTTATACT
          Q  R  P   G  Q  G   L  E  W  I   G  Y  I   N  P  T   T  G  Y  T

181      AAGTACAATC AGAAGTTCAA GGACAAGGCC ACATTGACTG CAGACAAATC CTCCAGCACG
          K  Y  N   Q  K  F   K  D  K  A   T  L  T   A  D  K   S  S  S  T

241      GCCTACATGC AACTGAGCAG CCTGACCAAT GTGGACTCTG CAGTCTATTA TTGTACAACT
          A  Y  M   Q  L  S   S  L  T  N   V  D  S   A  V  Y   Y  C  T  T

301      GGTTACTCTT ATTTTGACTA CTGGGGCCAA GGGACCACGG TCACCGTCTC CTCAGGTGGA
          G  Y  S   Y  F  D   Y  W  G  Q   G  T  T   V  T  V   S  S  G  G

361      GGCGGTTCAG GCGGAGGTGG CTCTGGCGGT GGCGGATCGG ACATCGAGCT CACTCAGTCT
          G  G  S   G  G  G   G  S  G  G   G  G  S   D  I  E   L  T  Q  S

421      CCAGCAATCA TGTCTGCATC TCCAGGGGAG AAGGTCACCA TAACCTGCAG TGCCAGCTCA
          P  A  I   M  S  A   S  P  G  E   K  V  T   I  T  C   S  A  S  S

481      AGTGTAAATT ACATGCACTG GTTCCAGCAG AAGCCAGGCA CTTCTCCCAA ACTCTGGATT
          S  V  N   Y  M  H   W  F  Q  Q   K  P  G   T  S  P   K  L  W  I

541      TCTAGCACAT CCAACCTGGC TTCTGGAGTC CCTGCTCGCT TCAGTGGCAG TGGATCTGGG
          S  S  T   S  N  L   A  S  G  V   P  A  R   F  S  G   S  G  S  G

601      ACCTCTTACT CTCTCACAAT CAGCCGGATG GAGGCTGAAG ATGCTGCCAC TTATTACTGC
          T  S  Y   S  L  T   I  S  R  M   E  A  E   D  A  A   T  Y  Y  C

661      CAGCAAAGGA GTAGTTACCC ATACACGTTC GGAGGGGGCA CCAAGCTGCA AATCAAACGG
          Q  Q  R   S  S  Y   P  Y  T  F   G  G  G   T  K  L   Q  I  K  R

721      GCGGCCGCAG GTGCGCCGGT GCCGTATCCG GATCCGCTGG AACCGCGTGC CGCATAG
          A  A  A   G  A  P   V  P  Y  P   D  P  L   E  P  R   A  A  -
```

Fig. 2a

```
  1  ATGGCCCAGG  TCAAACTGCA  GCAGTCTGGG  GCTGAACTGG  CAAAACCTGG  GGCCTCAGTG
     M   A   Q   V   K   L   Q   Q   S   G   A   E   L   A   K   P   G   A   S   V

61  AAGATGTCCT  GCAAGACTTC  TGGCTACACC  TTTACTAGCT  ACTGGATGAA  CTGGGTAAAA
     K   M   S   C   K   T   S   G   Y   T   F   T   S   Y   W   M   N   W   V   K

121  CAGAGGCCTG  GACAGGGTCT  GGAATGGATT  GGATACATTA  ATCCTACCAC  TGGTTATACT
     Q   R   P   G   Q   G   L   E   W   I   G   *Y*  *I*  *N*  *P*  *T*  *T*  *G*  *Y*  *T*

181  AAGTACAATC  AGAAGTTCAA  GGACAAGGCC  ACATTGACTG  CAGACAAATC  CTCCAGCACG
     *K*  *Y*  *N*  *Q*  *K*  *F*  *K*  *D*  K   A   T   L   T   A   D   K   S   S   S   T

241  GCCTACATGC  AACTGAGCAG  CCTGACCAAT  GTGGACTCTG  CAGTCTATTA  TTGTACAACT
     A   Y   M   Q   L   S   S   L   T   N   V   D   S   A   V   Y   Y   C   T   T

301  GGTTACTCTT  ATTTTGACTA  CTGGGGCCAA  GGGACCACGG  TCACCGTCTC  CTCAGGTGGA
     *G*  *Y*  *S*  *Y*  *F*  *D*  *Y*  W   G   Q   G   T   T   V   T   V   S   S   G

361  GGCGGTTCAG  GCGGAGGTGG  CTCTGGCGGT  GGCGGATCGG  ACATCGAGCT  CACTCAGTCT
     G   G   S   G   G   G   S   G   G   G   S   D   I   E   L   T   Q   S

421  CCAGCAATCA  TGTCTGCATC  TCCAGGGGAG  AAGGTCACCA  TAACCTGCAG  TGCCAGCTCA
     P   A   I   M   S   A   S   P   G   E   K   V   T   I   T   C   *S*  *A*  *S*  *S*

481  AGTGTAAATT  ACATGCACTG  GTTCCAGCAG  AAGCCAGGCA  CTTCTCCCAA  ACTCTGGATT
     *S*  *V*  *N*  *Y*  *M*  *H*  W   F   Q   Q   K   P   G   T   S   P   K   L   W   I

541  TCTAGCACAT  CCAACCTGGC  TTCTGGAGTC  CCTGCTCGCT  TCAGTGGCAG  TGGATCTGGG
     S   *S*  *T*  *S*  *N*  *L*  *A*  *S*  G   V   P   A   R   F   S   G   S   G   S   G

601  ACCTCTTACT  CTCTCACAAT  CAGCCGGATG  GAGGCTGAAG  ATGCTGCCAC  TTATTACTGC
     T   S   Y   S   L   T   I   S   R   M   E   A   E   D   A   A   T   Y   Y   C

661  CAGCAAAGGA  GTAGTTACCC  ATACACGTTC  GGAGGGGGCA  CCAAGCTGCA  AATCAAACGG
     *Q*  *Q*  *R*  *S*  *S*  *Y*  *P*  *Y*  *T*  F   G   G   G   T   K   L   Q   I   K   R

721  GCGGCCGCAG  GTGCGCCGGT  GCCGTATCCG  GATCCGCTGG  AACCGCGTGC  CGCATAG
     A   A   A   G   A   P   V   P   Y   P   D   P   L   E   P   R   A   A   -
```

Fig. 2b

SINGLE CHAIN ANTIBODY AGAINST MUTANT P53

RELATED APPLICATION

This Application is a continuation of U.S. patent application Ser. No. 09/526,738 filed on Mar. 16, 2000, now U.S. Pat. No. 6,630,584 issued on Oct. 7, 2003. The contents of the above application are incorporated herein by reference.

FIELD OF THE INVENTION

This invention relates to single chain antibody molecules against the p53 gene product.

BACKGROUND OF THE INVENTION

The following references are referenced in the specification and may be relevant to understanding the invention:
1. Gamble, J. and Milner, J. (1988). Evidence that immunological variants of p53 represent alternative protein conformations. *Virology*, 162, 452-458.
2. Harlow, E., Crawford, L. V., Pim, D. C. and Williamson, N. H. (1981). Monoclonal antibodies specific for simian virus 40 tumor antigens. *J. Virol*, 39, 861-869.
3. Yewdell, J. W., Gannon, J. V. and Lane, D. P. (1986). Monoclonal antibody analysis of p53 expression in normal and transformed cells. *J. Virol*. 59, 444-452.
4. Milner, J., Cook, A. and Sheldon, M. (1987). A new anti-p53 monoclonal antibody, previously reported to be directed against the large T antigen of simian virus-40. *Oncogene*, 1, 453-455.
5. Gannon, J. V., Greaves, R., Iggo, R. and Lane, D. P. (1990). Activating mutations in p53 produce common conformation effects. A monoclonal antibody specific for the mutant form. *EMBO J*. 9, 1595-1602.
6. Marasco, W. A. (1995) Intracellular antibodies (intrabodies) as research reagents and therapeutic molecules for gene therapy. *Immunotechnology*, 1, 1-19.
7. Stephen. C. W. and Lane, D. P. (1992). Mutant conformation of p53 precise epitope mapping using a filamentous phage epitope library. *J Mol Biol*. 225, 577-583.
8. Jannot. C. B. and Hynes, N. E. (1997). *Biochem. Biophys. Res. Commun.*, 230, 242-246.
9. Cohen, P. A., Mani, J. C. and Lane, D. P. (1998). Characterization of a new intrabody directed against the N-terminal region of human p53. *Oncogene*, 17, 2445-2456.

The p53 gene encodes a protein which is 53 kD in size (hence the name). The p53 protein is situated in the nexus of intermingled pathways controlling cell proliferation, cell survival and differentiation. It can sense and integrate various external and internal stimuli, such as DNA damage, hypoxia, oxidative stress, deregulated oncogene expression and ribonucleotide depletion. In response to these stimuli, it may trigger cell cycle arrest, apoptosis, senescence, differentiation or antiangiogenesis. It appears that the p53 protein is involved in regulation of critical growth controlling checkpoints. It is capable of exercising a tumor suppressor function by preventing cells, that are in unfavorable environmental conditions or are carrying damaged DNA, from entering a cell cycle.

Mutations within the p53 gene have been found in more than 50% of all human cancers, rendering it the most frequently mutated single gene in human cancer known so far. Most of the mutations in the p53 gene discovered in cancers are of a missense type. They cause not just abrogation of the tumor suppressor function of wild-type p53, but often actively contribute to the tumor transformation function of mutant p53. Inactivation of p53 is one of the most common molecular events in cancer development.

As mentioned above, the p53 protein, which is both a regulator for cell proliferation and a suppressor of tumor development, can prevent the development of cancer by blocking the division of cells which have sustained DNA damage, or by triggering apoptosis. It has been proposed that the effect of mutant p53 on tumor progression is due to a dominant negative interaction of the wild type and mutant proteins. Thus, wild-type and mutant p53 proteins are respectively capable of contrasting suppressor and promoter effects on tumor development.

The ability of p53 to act both as a suppressor and a promoter of tumor development may reflect the ability of the protein to adopt different conformations. Mitogenic stimulation of primary T cells induces a change in the immunoreactivity of p53 and this may be due to a change in the tertiary structure of the p53 protein. To ascertain whether the 'mutant' conformation of wild-type p53 has physiological relevance, attempts have been made to associate it with a biochemical activity. Conformation-specific monoclonal antibodies, previously shown to discriminate between wild-type and mutant p53 proteins, have been used to demonstrate structural changes in wild-type p53 following sequence-specific binding to DNA (1). These studies suggested that wild-type p53 can physiologically adopt distinct conformations, which determine its DNA binding activity. Mutations that render p53 oncogenic may lock p53 into one of the few conformational states it physiologically adopts, rather than distort its tertiary structure.

Two important cellular factors appear necessary for this conversion: (1) binding of an 'activating' polypeptide that causes neutralization of the C-terminal negative regulatory domain, and (2) a highly reduced environment which can maintain p53 in an activated state. Given the clear association between the DNA binding activity and tumor suppressor functions of p53, these results imply that in many tumor cells there are high levels of mutant p53 that can potentially be activated to restore significant wild type function.

A variety of monoclonal antibodies have been prepared against various epitopes of p53.

A panel of anti-p53 mouse monoclonal antibodies has been used to characterize the immunoreactivities of the native p53-Ala35 and the mutant p53-Val 35 translated under various conditions. Two monoclonal antibodies, PAb421 and PAb248, were able to recognize discrete denaturation-stable epitopes on the p53-polypeptide (2,3). These antibodies immunoprecipitated both p53-Ala35 and p53-Val 35 translated at 30° C. and 37° C., and were also able to immunoprecipitate p53 from a variety of murine cell lines (4).

Three additional monoclonal antibodies, PAb246, PAb 1620 and PAb240, were found to detect conformational changes in the p53 protein (5). Molecules in the mutant conformation are distinguished from wild-type molecules, inter alia, by the appearance of a new, normally cryptic epitope recognized by Pab240. This epitope was localized to residues 213 to 217 of the p53 protein and has the sequence RHSVV, preceded by F in human and mouse p53 (7). More than 90% of mutations found in p53 produce a conformational change in the p53 protein which results in the exposure of this epitope, which is otherwise hidden in the hydrophobic core of the molecule. This epitope will be referred to hereinafter as the common mutant epitope of p53.

Recent advances in antibody engineering have allowed the genes encoding antibodies to be manipulated, so that antigen binding molecules can be expressed within mammalian cells in a controlled way (6). Application of gene technologies to antibody engineering has enabled the synthesis of single-chain fragment variable (scFv) antibodies that combine within a single polypeptide chain the light and heavy chain variable domains of an antibody molecule covalently joined by a predesigned peptide linker. The resultant scFv gene can be expressed in bacterial expression systems such as E. coli. Bundled in the "gene display package" single-chain antibodies displayed at the surface of filamentous phages of the M13 family provided the possibility to create antibody libraries both from various living sources and products of diversification of a single scFv molecule. Antibodies with the desired specificity can be isolated from such libraries employing effective selection techniques (biopanning) in which the antigen is immobilized on a solid support.

The ability to create scFv antibodies, when combined with their stable expression in precise intracellular locations in mammalian cells, has enabled the creation of a powerful new family of antibody molecules for basic research or gene therapy. These intracellular antibodies (intrabodies) can be used to modulate cellular physiology and metabolism through a variety of mechanisms, including the blocking, stabilizing or mimicking of protein-protein interactions, by altering enzyme function, or by diverting proteins from their usual intracellular compartments. Intrabodies can be directed to the relevant cellular compartments by modifying the genes that encode them to specify N- or C-terminal polypeptide extensions for providing intracellular-trafficking signals. This approach has been described for a number of different antigens, including several HIV proteins.

Several scFv antibodies against p53 have been previously described. The scFv-421 antibody recognizes a C-terminal epitope of the protein (8). When expressed in vitro in the cytoplasm or in the nucleus of COS-1 cells, it was found to be non-functional and prone to rapid degradation. An important determinant of correct antibody folding is the formation of intra-chain disulfide bonds in the variable regions; possibly the reducing environment of the cytosol may lead to a decrease in the stability of the scFv (9). Nevertheless, some scFv antibodies have been expressed in the cytoplasm and shown to have biological effects, indicating that other features, such as the primary sequence of the antibody and/or its specific cellular location may be important for their proper function.

The scFv DO-i antibody was found to recognize an N-terminal epitope of human p53 (9). The DO-1 scFv was targeted to the cytoplasm and to the nucleus of mammalian cells. Interestingly, insertion of the $C_K$ domain into scFv to create a scFv$C_K$ fusion protein, led to a dramatic increase in the level of intracellular expression. However, in other studies in which $C_K$ fusions to scFv were made, the effects on stability and expression were much less marked. It is clear that each scFv is a particular and individual case (9).

SUMMARY OF THE INVENTION

It is an object of the present invention to provide a single chain antibody which recognizes an epitope exposed on mutant, but not on wild-type, p53.

Thus, in a first aspect the present invention provides a DNA molecule encoding a single chain antibody (scFv) which specifically recognizes the common mutant epitope in mutant p53 but not in wild type p53.

In a preferred embodiment, the scFv is ME1.

In a most preferred embodiment, the DNA molecule of the invention comprises SEQ. ID. NO. 1.

In the present specification, the normally cryptic, mutant p53 epitope motif as described above (FRHSVV SEQ ID NO: 8) which is recognized by the Pab240 antibody (7) is termed the "common mutant epitope" of mutant p53. This epitope differs from the p53 epitopes recognized by the previously disclosed scFv antibodies mentioned above.

In order to realize the object of the invention, the gene segments encoding variable parts of the antibody heavy and light chains were amplified by PCR from the spleen of the hyperimmunized mouse, and a library of the antibody genes was obtained. When the genes isolated from the antibody gene library were assembled in the scFv DNA, expressed as phage antibodies and subjected to panning, the single-chain scFv ME1 that was isolated possessed a significant affinity ($10^{-7}$ M) towards mutant p53 and was successfully expressed as a soluble antibody, separate from the phage fusion.

Such libraries usually contain a large number of different genes encoding the antibodies specific to the chosen antigen, in contrast to a single pair ($V_H$ and $V_L$) of antibody genes encoding a single antibody as present in hybridoma cells. This issue has a special importance for the amplification of mouse antibody genes because the sequencing of their repertoire has not yet been completed, and thus it is still not possible to design a primer set covering all existent antibody gene variants. Also, some single-chain antibody genes are difficult to express in bacterial cells for various reasons, among which are their toxicity for the host, low conformational stability and rapid proteolytic degradation. Thus, it appears that a much improved starting point for scFv construction is selecting from the collection of variants of the $V_H$ and $V_L$ domains present in the immunized host, than from a hybridoma cell line.

One or more nucleotides of the DNA molecule of the invention may be modified without affecting the ability of the antibody, encoded by the modified DNA molecule, to specifically recognize the common mutant epitope in mutant p53 but not in wild type p53. Such modifications are well known to the skilled man of the art, and include (1) substitutions, e.g. based on the degeneracy of the genetic code, and (2) insertions or deletions of nucleotide base triplets resulting in insertions to or deletions from the amino acid sequence of the scFv at non-essential locations. The modifications may be carried out by various techniques such as site-directed mutagenesis.

Codons preferred by a particular prokaryotic or eukaryotic host (Murray, E. et al. Nuc Acids Res., 17:477-508, (1989)) can be selected, for example, to increase the rate of variant product expression or to produce recombinant RNA transcripts having desirable properties, such as a longer half-life, than transcripts produced from naturally occurring sequence. In a further preferred embodiment of this aspect of the invention, the DNA molecule comprises SEQ. ID. NO: 3, which has been modified for eukaryotic expression.

The DNA sequence of the present invention can be engineered in order to alter a scFv product coding sequence for a variety of reasons, including but not limited to, alterations which modify the cloning, processing and/or expression of the product. For example, alterations may be introduced using techniques which are well known in the art, e.g., site-directed mutagenesis, to insert new restriction sites, to alter glycosylation patterns, to change codon preference, etc.

The invention also relates to a vector, such as a plasmid or viral vector, into which the DNA molecule of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available. A preferred vector is the expression vector pIRES-EGFP-ME 1.

The present invention also relates to host cells which are genetically engineered with vectors of the invention, and the production of the product of the invention by recombinant techniques. Host cells are genetically engineered (i.e., transduced, transformed or transfected) with the vectors of this invention which may be, for example, a cloning vector or an expression vector., The vector may be, for example, in the form of a plasmid, a viral particle, a phage, etc. The engineered host cells can be cultured in conventional nutrient media modified as appropriate for activating promoters, selecting transformnants or amplifying the expression of the variant nucleic acid sequence. The culture conditions, such as temperature, pH and the like, are, those previously used with the host cell selected for expression, and will be apparent to those skilled in the art. A preferred host cell is a mammalian host cell containing the pIR-ES-EGFP-ME1 vector.

In a second aspect, the invention provides scFv molecule which specifically recognizes the common mutant epitope in mutant p53 but not in wild type p53.

In a preferred embodiment, the scFv is ME1

In a most preferred embodiment, the scFv comprises the amino acid sequence SEQ. ID. NO. 2. In another preferred embodiment, the scFv comprises SEQ. ID. NO: 4.

One or more amino acids of the scFv of the invention may be modified without affecting the ability of the antibody to specifically recognize the common mutant epitope in mutant p53 but not in wild type p53. Such modifications are well known to the skilled man of the art, and include (1) substitutions, e.g. substituting hydrophilic or hydrophobic amino acids with other hydrophilic or hydrophobic amino acids, respectively, by site directed mutagenesis, (2) insertions or deletions of amino acids at non-essential locations, and (33) chemical modifications.

Thus, the invention also includes a polypeptide comprising a polypeptide sequence having, at least a 95% sequence identity, and more preferably at least a 99% sequence identity, to SEQ. ID. NO.2, wherein said polypeptide sequence, specifically recognizes the common mutant epitope in mutant p53 but not in wild type p53.

The modifications of the DNA molecule or of the scFv molecule may be directed towards conferring upon the scFv polypeptide various characteristics such as (1) increased specificity for the mutant p53 molecule as compared to the wild type p53 molecule, (2) higher affinity for the mutant p53 antigen, (3) increased stability and resistance to proteolysis, (4) enhanced expression and solubility of the scFv antibody in vitro and in vivo, and (5) preferred targeting of the scFv antibody to sub-cellular sites by incorporation into the scFv antibody of, for example, ER and nuclear targeting peptide sequences, so as to generate preferred embodiments of the invention for pharmacological and pharmaceutical applications. An example of a domain of the scFv which may be modified is the CDR domain. These alterations can be achieved not only by the introduction of nucleotide changes in the cloned scFv antibody gene encoding the polypetide using commonly known methods of chemical and enzymatic mutagenesis, such as oligonucleotide-directed mutagenesis and PCR-based mutagenesis (see Current Protocols in Molecular Biology, John Wiley and Sons, Inc., 1997, Volume 1, section 8), but also by chemical changes in the amino acid sequence of the scFv, such as glycosylation and by the creation of polyvalent scFv antibodies (see Smythe J. A. et al., (1994) Protein Engineering 7:145-147).

The scFv antibody of the invention has distinct advantages over the existing monoclonal antibodies. Thus, the modifications outlined above can readily be made with the scFv antibody but not with the monoclonal antibody. The smaller size of the scFv is also an advantage in intracellular applications.

In a third aspect, the invention provides a pharmaceutical composition comprising either a DNA molecule, a vector, or an antibody molecule according to the invention, and a pharmaceutically acceptable excipient.

In a fourth aspect, the invention provides a method for treating a patient suffering from a disease whose etiology is related to a mutation in the p53 gene comprising administrating to said patient a pharmaceutical composition according to the invention.

The scFv of the invention may be useful in the treatment of a disease whose etiology is related to a mutation in the p53 gene, and in particular. in the treatment of cancer.

A novel and promising approach in the gene therapy of tumors lies in the intracellular expression of antibodies that are capable of inactivating certain oncogene products, or by targeting their degradation. Because mutant p53 exerts distinct oncogenic properties and appears in the cytosol of a wide range of tumors, an intracellularly expressed single-chain antibody (intrabody) directed against this protein may serve as a "broad spectrum" agent for tumor therapy. To adapt the ME1 scFv for conditions of intracytosolic mammalian expression, several modifications were introduced in the scFv DNA, as will be described more particularly below.

The scFv ME1 of the invention may serve as a powerful auxiliary agent capable of significantly enhancing the specificity and effectiveness of the two major existent anti-cancer gene therapies.

One of these strategies employs an overexpression of the wild-type p53 protein in cancer cells. In spite of the promising results obtained from several clinical trials utilizing this technique, it was recently found that cancer cells containing a mutant form of p53 are largely recalcitrant to this treatment. Expression of the scFv ME1 molecule as an intrabody fused to the F-box domain responsible for the targeting of the cell proteins to the degradation cascade may be capable of significantly reducing the level of mutant p53 in the cell, thereby broadening the range of possible tumor targets for the original therapy.

Another emerging anti-cancer gene therapy employs a single-chain antibody directed to a p53 protein epitope which is present both in wild-type and mutant p53 molecules: It forms a part of the synthetic transcription factor containing also the bacterial tetracycline repressor as a DNA binding domain. The strategy is based on the fact that the mutant form of p53 antibody serve as a tether bringing together a transactivation function provided by p53 and the DNA binding activity from the tetracycline receptor. The resultant complex can activate the transcription of the protein toxin put under control of the promoter containing tetracycline-operator sequences. The major drawback of this strategy is the indiscriminate nature of the antibody employed which causes an activation of toxin expression in a cell containing any form of p53 protein. As a consequence, only the local administration of this treatment can be considered as safe. The substitution of the original antibody by the scFv ME1 specific to the mutant form of p53 may restrict the therapeutic effect to cancer cells only, allowing a systemic application of this therapy.

In addition to its clinical importance, the scFv ME1 antibody can serve as a valuable research and diagnostic tool, allowing specific tagging of mutant p53 molecules inside the cell. Mutation of the p53 gene results in stabilization of the protein and a subsequent increase in intracellular protein sufficient to be detectable by immunohistochemistry. The high specificity of the scFv of the invention towards a peptide epitope, which appears only in mutant variants of p53, the lack of the Fc portion which binds specifically to the antigen, and the high permeability of these small antibodies into cells, make the antibody of the invention a suitable probe for immunodiagnostic clinical detection of mutant p53 in tissues, using conventional immunohistochemistry techniques. An immunodiagnostic kit could therefore be prepared comprising the scFv of the invention. Such kits using other antibodies for detecting other antigens are well known in the art.

DETAILED DESCRIPTION OF THE DRAWINGS

Figure 1B:
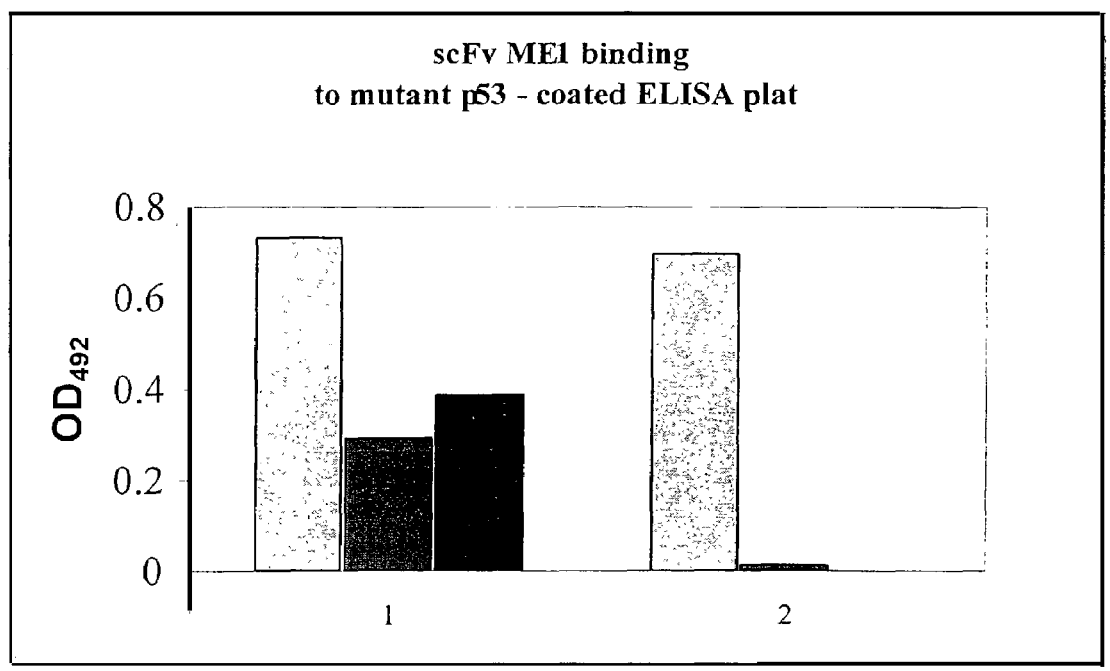
Figure 3:
Figure 4:
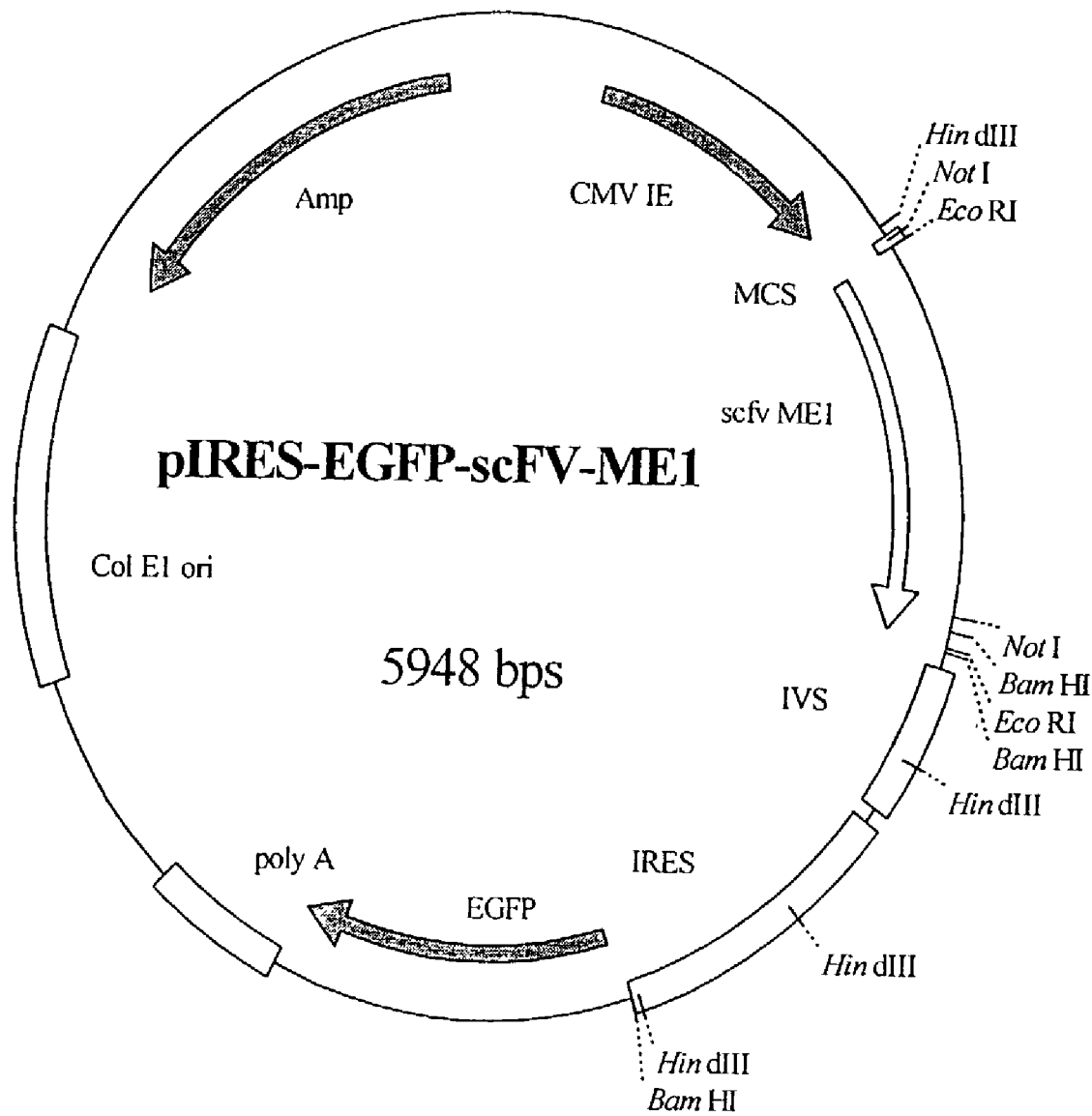

In order to understand the invention and to see how it may be carried out in practice, a preferred embodiment will now be described, by way of non-limiting example only, with reference to the accompanying drawings, in which:

FIG. 1A is a diagram displaying binding of (1) the monoclonal antibody PAb 240; (2) soluble ME1 scFv; (3) phage displayed ME1 scFv; and (4) unrelated phage scFv, to a mutant p53 cated ELISA plate;

FIG. 1b is a diagram displaying binding of (1) the phage displayed ME1 scFv, and (2) monoclonal antibody PAb 240, to mutant p53 coated ELISA plates in the presence (grey bars) or absence (stippled bars) of the mutant p53 protein and in the presence of 100 µg/ml (black bar) of the epitopic peptide FHRSVV FIG. 2a shows the nucleotide (SEQ. ID. NO:1) and amino acid (SEQ. ID. NO: 2) sequences of the ME1 single-chain antibody specific to the common mutant epitope of the mutant p53 protein. Underlined—parts of the amino acid sequence that come from the primers and linker DNA; Italics—CDR1; Underlined italics—CDR2; Underlined bold italics—CDR3; Bold D—first amino acid of the light chain;

FIG. 2b shows the nucleotide (SEQ. ID. NO:3) and amino acid (SEQ. ID. NO: 4) sequences of the ME1 single-chain antibody of FIG. 2a modified for eukaryotic expression. The symbols are as in FIG. 2a;

FIG. 3 illustrates detection of the ME1 scFv by Western blot with an antibody specific to the svFv E-tag. From left to right: periplasmic extract of the ME1 scFv expression *E. coli* HB2151 cells; periplasmic extract of the control scFv expressing *E. coli* XL-1 cells; whole cell extract of the MI1 scFv expressing *E. coli* HR2151 cells; whole cell extract of the control scFv expression *E. coli* XL-1 cells;

FIG. 4—The pIRES-EGFP-ME1 expression vector map; and

Figure 5:
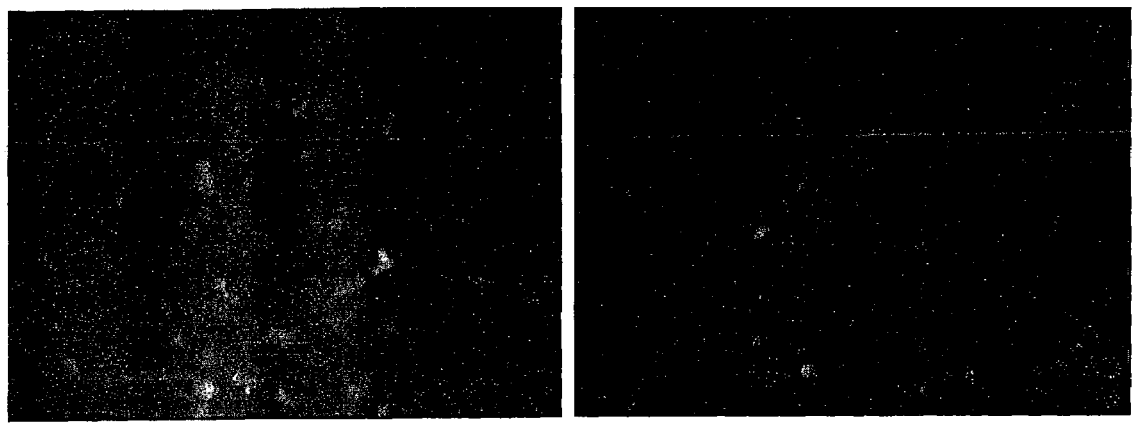

FIG. 5—EGFP fluorescence in 293 cells transfected with a) the pIRES-EGFP-ME1 scFv construct and b) the pIRES-EGFP vector alone. The insertion of the ME1 scFv DNA into the vector shifted a translation initiation of the EGFP to the attenuated IRES that lead to a reduced rate of the EGFP synthesis and decreased level of the EGFP fluorescence in comparison with cells transfected with the vector alone.

DETAILED DESCRIPTION OF A PREFERRED EMBODIMENT

A. MATERIAL AND METHODS

I. Covalent-coupling of the epitopic peptide to microfiter plates

Originally, the KFRHSVV heptapeptide (SEQ ID NO: 5) was obtained as a crude preparation after the peptide synthesis at Weizmann Institute. The N-terminal lysine (K) was added to the native hexapeptide sequence in order to facilitate a covalent coupling through an e-amino group of the lysine to the active groups of the solid support.

Peptide purification was performed on the Gilson-301 HPLC chromatographer (Gilson, France) using the 5 µm Lichrosorb RP-18 column (Dr. Herbert Knauer KG, Germany). 1 ml of 1 mg/ml solution of the crude peptide preparation was applied to the column pre-equilibrated with 0.1% trifluoroacetic acid in water (Solution A). The elution was carried out with a linear gradient of 0 to 100% of solution B (80% acetonitrile in solution A) for 70 min at flow rate of 1 ml/min. The effluent was monitored in UV light detector at 230 nm. The peak fractions were pooled and dried in a SpeedVac. The fractions that revealed the presence of the heptapeptide (as determined by amino acid analysis at Weizmann Institute) were selected for the subsequent work.

Covalent binding of the heptapeptide to microtiter plates. 96-wells microtiter plates (Nunc, Denmark) were coated with the epoxy-activated polymeric carrier Eupergit C (Rohm, Germany) according to the prescription of the manufacturer. 200 µl of 0.2 M 1,4-Adipic acid dihydrazide (Sigma, USA) in 0.2 M carbonate buffer, pH 9.0 were added per well of the Eupergit C-coated plates. After 16 hours of incubation at room temperature, the plates were emptied, filled with 250 µl of the blocking solution (0.2 M mercaptoethanol in PBS) per well and kept overnight at 4° C. At the next step, the blocking solution was removed and plates were activated by adding of 200 µl per well of 25% glutaraldehyde solution in water (Merck, Germany) and incubating for 2 hours at room temperature. After removal of the glutaraldehyde solution, the activated plates were filled with 100 µl per well of the purified peptide dissolved in PBS and incubated for 2 hours at room temperature. The wells content was replaced subsequently with 200 µl of the blocking solution containing 1% of non-fat, dry milk and incubated overnight at 4° C. Following the incubation, the plates were washed thoroughly, dried, sealed under vacuum in the plastic bags and stored at −20° C.

The mutant p53 protein and BSA-heptapeptide conjugate were covalently bound to the Eupergit C-coated microtiter plates by incubation of the protein dissolved in 1 M of Kpi (potassium-phosphate buffer, pH 8.0), followed by overnight incubation in the blocking solution at 4° C.

ELISA test. All ELISA tests in this project were performed in 96-wells microtiter plates (Costar). Border wells were excluded from the analysises. 100 µl of primary antibodies were routinely applied to each well under the test. Primary antibodies were diluted two-fold either with PBS containing 10% of non-fat dry milk or BSA. The incubation conditions were 1 hour at 37° C. for the monoclonal antibody PAb 240 culture liquid supernatant, 2 hours at 37° C. or overnight at 4° C. for the phage antibody supernatant or periplasmic extract containing soluble antibodies.

To perform the competitive ELISA test, the diluted primary antibody was pre-incubated with the antigen for one hour at 37° C. with intermittent shaking. The horseradish peroxidase (HRP)-conjugated rabbit anti-mouse IgG (Sigma, USA) antibody diluted 1:2500 or HRP-conjugated goat anti-M13 phage antibody diluted 1:5000 (Pharmacia, Sweden) were employed as a secondary antibody. The incubation conditions for a secondary antibody were one hour at 37° C. Between the incubations plates were washed four times in PBS containing 0.05% Tween 20 followed by four washes in PBS. To develop ELISA reaction, 30 µg of o-phenylenediamine dihydrochloride (Sigma, USA) was dissolved in 15 ml of 0.05M citrate buffer, pH 5.0, combined with 4 µl of 30% $H_2O_2$ were applied in 100 µl aliquotes to each well under the test. After developing of yellow color, the reaction was stopped by introducing 50 µl of 4 N HCl into each well. The plates were scanned in the EasyReader 400 FW ELISA reader (SLT, Austria) at 492 nm with reference at 405 nm.

II. Cloning, Construction and Phage Display of scFv from the Spleen of Hyperimmunized Mouse Immunization protocol—Five female BALB/c mice were immunized with the mutant p53 epitope peptide conjugated to BSA and boosted with the conjugate. To follow the course of the immunization, mice were bled and policlonal sera were prepared according to Harlow E. Lane D. (1988) Antibodies: Laboratory Manual. Cold Spring Harbor Laboratory Press, NY, USA. Titers of the antibodies specific to the conjugated and non-conjugated heptapeptide were measured in ELISA assay as described in Section I.

Splenocyte isolation—To obtain splenocytes, a mouse with the highest specific antibody titer was sacrificed, its spleen was aseptically removed and cut into small pieces. 25 ml of sterile DMEM with high glucose (4.5 g/l) (Biological Industries (Israel)) supplemented with 10% heat inactivated (56° C., 30 min) horse-serum (Biological Industries, Israel), 4 mM L-glutamine (Biological Industries, Israel), 100 U/ml penicillin and streptomycin solution (Biological Industries, Israel) were added to the minced spleen and pipetted through a large-bore sterile pipet. The spleen cell suspension was transferred into a sterile 50 ml centrifuge tube and cells were pelleted at 800×g in a Sorvall GLC-4 centrifuge for 5 min. The supernatant was discarded and the cell pellet was stored at −70° C.

mRNA isolation—mRNA isolation from the splenocytes was accomplished with the help of the QuickPrep mRNA Purification Kit (Pharmacia, Sweden) according to the manufacturer's instructions.

III. Construction of the single-chain antibody (scFv)

A scFv gene fragment was constructed with the help of the Recombinant Phage Antibody System Kit (Mouse scFv Module) of Pharmacia (Sweden) according to manufacturer protocols.

First-Strand cDNA Synthesis—The RNA sample ($OD_{260}$-0.02) was spun for 10 min in a desktop centrifuge at −4° C. The precipitate was washed two times with cold (−20° C.) 95% ethanol dried and dissolved in 20 µl of DEPC-treated water. Two aliquots (each of 5 µl) of the mRNA solution were placed in 0.5 ml microcentrifuge tubes, heated at 65° C. for 10 min. For each aliquot the following reaction mixture was prepared in 0.5 ml tubes (one tube for the antibody light chain and another for the antibody heavy chain): 16 µl of DEPC-treated water, 11 µl of primed first-strand mix (recombinant Moloney Murine Leucosis Virus reverse transcriptase, random hexadeoxyribonucleotides, RNAguard, RNase/DNase-free BSA, dATP, dCTP, dGTP, and dTTP in aqueous buffer) and 1 µl of 200 mM DTT solution. Aliquots of the mRNA were cooled briefly on ice after heating, added to the reaction mixture and incubated for 1 h at 37° C.

Primary PCR Amplification—The following mixtures were prepared in 0.5 ml tubes for the light chain PCR −2 µl of Light primer mix (mixture of 10 variable light chain primers in water) and 64 µl of sterile distilled water; for the heavy chain PCR −2 µl of Heavy primer 1 (upstream primer in water), 2 µl of Heavy primer 2 (downstream primer in water) and 62 µl of sterile distilled water. To each tube 33 µl of first-strand reaction mixture were added and overlaid with 0.1 ml of mineral oil. The tubes were placed in a thermocycler and heated at 95° C. for 5 min. 1 µl of AmpliTaq DNA polymerase of 5000 U /ml (Perkin-Elmer Cetus, USA) was added to each tube. The PCR reaction was run with a program as follows: 30 cycles—94° C. for 1 min; 55° C. for 2 min; 72° C. for 2 min.

Purification of Primary PCR Products—Purification of PCR products was performed by gel electrophoresis in 1.5% agarose gel (50 µl of each PCR mixture per well). Molecular weight markers were 100 Base-Pair Ladder mixture (Pharmacia, Sweden) and the HaeIII digest of φ174 RF (Eastman-Kodak, USA). The DNA bands of 340 and 325 bp (corresponding to heavy and light chain respectively) were excised and the DNA purified by Sephaglas Bandprep Kit Pharmacia, Sweden). The DNA was dissolved in 20 µl of Tris-HCl (pH 8.3), 0.1 M EDTA buffer (TE buffer) and stored at −20° C.

Gel quantitation of purified product and inner fragment—Aliquots (2 µl) of each DNA sample and 2 µl of Linker-Primer mix (equimolar mixture of 3' heavy and 5' light linker primers in water) were electrophoresed in 1.5% agarose. BstEIII digest and HindIII digests of lambda DNA were used as standards. Relative amounts of heavy and light chain products and the linker-primer DNA were estimated visually after staining with ethidium bromide solution.

Assembly and Fill-in Reactions —The following reaction mixtures were prepared in 0.5 ml tubes: 0.5 µl of heavy chain product, 2 µl of light chain product, 1 µl of the linker-primer mix, 2.5 µl of 10×PCR buffer, 1.25 µl of dNTP Mix (20 mM each dNTP), 2.5 µl of 25 mM $MgCl_2$, 1 µl of AmpliTaq DNA Polymerase and 9.25 µl of sterile distilled water. The mixtures were overlaid with 25 µl of mineral oil. The tubes were placed in a thermocycler and run with a program: 20 cycles —94° C. for 1 min; 63° C. for 4 min.

Second PCR Amplification and Purification—A 75 µl mix was prepared containing 1.5 µl of AmpliTaq DNA Polymerase, 7.5 µl of 10 ×PCR buffer, 1.5 µl of dNTP Mix, 6 µl of RS Primer Mix (mixture of 5' heavy chain primer with SfiI site and 3' light chain primer with NotI site in water) and 58.5 µl of sterile distilled water. 25 µl of the mix was added to the assembly reaction, overlaid with 25 µl of mineral oil and run with the same program as above. After PCR 5 µl aliquots of the mixtures were analysed by electrophoresis in 1.5% agarose with a BstEII digest of lambda DNA as a standard. The 750 bp DNA band was excised and the DNA product was purified by Sephaglas Bandprep Kit. The purified DNA sample was dissolved in 20 µl of TE buffer and stored at −20° C.

PCR Amplification of Assembled Product—The following reaction mixture was prepared in three 0.5 ml tubes: 2 µl of the assembled single-chain DNA product from the previous procedure, 4 µl of RS primer Mix, 5 µl of 10×PCR buffer, 2.5 µl of dNTP mix, 5 µl of $MgCl_2$ solution (molarity of the solution was varied in different tubes) and 30.5 µl of sterile distilled water (17). The molarity of the $MgCl_2$ was varied as follows: 25 mM, 45 mM and 85 mM. Each mixture was overlaid with 50 µl of mineral oil and the tubes placed in a thermocycler for 5 min at 95° C. 1 µl of AmpliTaq DNA polymerase of 5000 U/ml was added to each tube. The PCR reaction was run using the program: 30 cycles –94° C. for 1 min; 55° C. for 2 min; 72° C. for 2 min. The amplified 750 bp band was separated by electrophoresis in 1.5% agarose gel and the DNA product isolated from the gel using Sephaglas Bandprep Kit. The purified DNA sample was dissolved in 20 μl of TE buffer and stored at –20° C.

Restriction Digestion—4 μl of the purified scFv DNA sample from the previous step was combined with the 5 μl of 10×SfiI buffer and 5 μl of the SfiI restriction enzyme (Pharmacia, Sweden). Total volume was adjusted to 50 μl with sterile distilled water and the mixture, overlayed with 50 μl of mineral oil, was incubated overnight at 50° C. A NotI restriction digest mix was prepared by mixing 2.5 μl of 5 M NaCl, 5 μl of 10×NotI buffer, 7.5 μl of NotI restriction enzyme and 35 μl of sterile distilled water. Total 50 μl of the mix were pipetted beneath the mineral oil layer of the SfiI digest and incubated overnight at 37° C. After the restriction digestion the sample was heated at 65° C. for 15 min. A MicroSpin Column loaded with the Sephacryl S-400 HR resin (Phannacia, Sweden) was equilibrated with the diluted ligation buffer (40 μl of the ligation buffer and 160 μl of sterile distilled water). The entire digested PCR product (excluding mineral oil) was applied to the MicroSpin Column and centrifuged at 800×g for 20 sec at 1.5 ml microcentrifuge tube. The effluent containing the purified scFv DNA was collected.

Ligation of the scFv gene into the pCANTAB 5E expression vector—25 μl of the scFv gene product was combined with 2μl of the 50 ng/μl solution of the pre-digested pCANTAB 5E expression vector DNA (Pharmacia, Sweden), 7 μl of ligation buffer and 3 μl of T4 DNA ligase (Gibco URL, USA). The mixture was incubated overnight at 16° C. in a 1.5 ml microcentrifuge tube.

Transformation—200 μl of electroporation-competent $E.$ $coli$ TG1 cells (prepared as described in Sambrook, J., Fritsch, E. F. & Maniatis, T. (1989). $Molecular\ Cloning.\ A$ $Laboratory\ Manual$. Cold Spring Harbor Laboratory Press, NY, USA) were transformed by 15 μl of the ligated phagemid-antibody scFv DNA using a Bio Rad Gene Pulser apparatus with the following settings: 25 μF, 2.5 kV at 200 ohms. The DNA preparation was desalted by drop-dialysis prior to the electroporation. Transformed cells were diluted with 800 μl of fresh SOC medium and incubated for 1 hour at 30° C. with shaking at 150 rpm. After the incubation, cells were plated onto SOB agar plates containing 100 μl of ampicillin and grown overnight at 30° C.

Rescue of the phagemid library from the plates—The plates were flooded with 5 ml of 2×YT medium (Sambrook, et al, op. cit.) and the colonies were resuspended by scraping with a sterile glass spreader, transferred to sterile 50 ml polypropylene tubes and diluted with 2×YT medium containing 100 μg/ml of ampicillin and 2M of glucose until an $A_{600}$ of 0.2-0.4 was reached. The diluted cells were grown at 37° C. with shaking at 200 rpm until an $A_{600}$ of 0.7 was achieved. Phage rescue was performed by infection of the cell suspension with $2.5 \times 10^9$ pfu per ml of the M13KO7 phage (Pharmacia, Sweden) and incubation for 30 min at 37° C. with shaking at 100 rpm, followed by a 30 min incubation with shaking at 200 rpm. The cells were pelleted by spinning in a clinical centrifuge (Sorvall GLC-4) at full speed for 10 min. The supernatant was discarded, whereas the pellet was resuspended in 1 ml of 2×YT medium containing 100 μg/ml of ampicillin and 50 μg/ml of kanamycin and transferred to sterile 17×100 mm culture tubes (Falcon) filled with 4ml of the medium used in pellet resuspension. After overnight incubation at 30° C. with shaking at 200 rpm, the cells were pelleted at full speed in a clinical centrifuge (Sorvall GLC-4) for 15 min and the supernatant containing the recombinant antibody phage was collected, filtered by passage through a 45 μm (Millipore) filter and stored in the sterile 17×100 mm culture tubes (Falcon) at 4° C.

Panning to select for antigen-positive recombinant phage antibodies—Four rounds of panning were performed in 96-well microtiter plates (Costar, USA) coated as described in Part I with 10 μg/ml of the BSA-heptapeptide conjugate. The phage supernatant was diluted two fold with PBS containing 1% of nonfat dry milk and applied by aliquotes of 200 μl to each well of the microtiter plates. After overnight incubation at 4° C., the plates were washed 10 times with PBS containing 0.2% of Tween 20 and 10 times with PBS. To elute the bound recombinant phage, 200 μl of log-phase TGI $E.\ coli$ cell suspension were added to each well and incubated with intermittent gentle shaking for 30 min at 37° C. After the incubation, contents of each well was collected and pooled together. Several aliquotes of 200 μl were taken from the combined pool, plated onto SOBAG plates (9) and incubated overnight at 30° C. The microtiter plates coated with 1 μg/ml and 0.1 μg/ml of the conjugate were employed for the fifth and sixth rounds of panning, respectively. The plates coated with 10 μg/ml of BSA were used as a negative control. In the second part of the panning procedure, two rounds of panning were performed on the microtiter plates coated with 1 μg/ml of the mutant p53 protein. Bacteriophage plaque counting assay was accomplished as in (Sambrook, et al, op. cit.).

Microtiter Plate Rescue of Enriched Phage Clones—100× μl of 2YT medium containing 100 μg/ml of ampicillin and 2% of glucose to each well on a sterile 96-well microtiter plate. Individual colonies were transferred to separate wells using sterile toothpicks and incubated overnight at 30° C. with gentle shaking (less than 100 rpm). 20 μl of saturated culture from each well were transferred to a corresponding well in the second microtiter plate. Each well of this plate was pre-filled with 180 μl of 2×YT medium containing 100 μg/ml of ampicillin, 2% of glucose and $10^8$ pfu of M13 KO7 phage. The second microtiter plate was incubated for 2 hours at 37° C. with shaking at 100 rpm. The contents of each well were transferred to individual 1.5 ml microcentrifuge tubes and pelleted at 1000×g for 10 min. Supernatants were discarded and pellets were resuspended in 200 μl of 2×YT medium containing 100 μg/ml of ampicillin and 50 μl of kanamycin. The tubes were incubated overnight at 30° C. with shaking at 100 rpm. After the incubation, the cells were pelleted as described above and supernatants were collected and transferred to the sterile microcentrifuge tubes and stored at 4° C.

PEG Precipitation Of The Phage Antibody Supernatant—1 ml aliquotes of the Phage antibody supernatant were mixed each with 200 μl of PEG-NaCl solution, incubated on ice for 1 hour and spun in an Eppendorf microcentrifuge for 30 min at 4° C. The supernatants were carefully aspirated and discarded. The pellets were resuspended with 10 μl of sterile TE buffer and stored at 4° C.

Infection of $E.\ coli$ HB2151 Cells—$E.\ coli$ HB2151 cells were grown to logarithmic phase in 5 ml of 2×YT medium. 200 μl of log phase cells were infected with 2 μl of the precipitated phage antibodies and incubated with gentle shaking for 30 min at 37° C. 20 μl aliquotes of the infected culture were plated onto SOBAG-N plates and grown overnight at 30° C.

Production of Soluble Antibodies—Several fresh colonies were selected from SOBAG-N plates. Each colony was transferred to 5 ml of SB-AG medium and incubated overnight at 30° C. with shaking at 200 rpm. The overnight culture was diluted to 50 ml with SB-AG medium and incubated for 1 hour at 30° C. with shaking at 200 rpm. The cells were pelleted by centrifugation at 1500×g for 15 min at room temperature in a Sorvall GLC-4 centrifuge, resuspended in 50 ml of SB-AI medium and incubated overnight with shaking at 200 rpm in 500 ml flasks. Each overnight culture was split into two equal aliquotes and centrifuged at 1500×g for 30 min at room temperature. The supernatants were collected, filtered through a 0.45 µm filter and stored at 4° C.

To prepare the periplasmic extract, one of the cell culture pellets was resuspended in 0.5 ml of PBS containing 1 mM of EDTA and incubated on ice for 30 min. The contents was transferred into a 1.5 ml microcentrifuge tubes and centrifuged at the highest speed in a microcentrifuge for 30 min at 4° C. The supernatant was carefully transferred to a clean tube and stored at −20° C.

To prepare the whole cell extract the second pellet obtained from the overnight culture was resuspended in 0.5 ml of PBS and boiled for 5 min. The cell debris was pelleted as described above, the supernatant was transferred to a clean tube and stored at −20° C.

The supernatant, periplasmic and whole cell extract fractions were analyzed for the presence of soluble antibodies in ELISA and Western blot assays. 10. Detection of Soluble Antibodies In Supernatant, Periplasmic Extract, and Whole Cell Extract—The detection was performed with the anti-E tag monoclonal antibody (Pharmacia, Sweden) specific to the peptide E tag located at, the C-terminal of single-chain antibody fragment expressed using the pCANT 5E vector. Electrophoresis and protein transfer were accomplished essentially as described in (Sambrook. et al, op. cit.). The ELISA and Western blot assay were carried out according to the anti-E tag antibody vendor instructions. The protein band visualization was performed by enhanced chemiluminescence method. The antigen-coated microtiter plates for the ELISA assay were prepared as described in the Part One.

DNA sequencing—The DNA sequence encoding the scFv ME1 antibody derived from the spleen of hyperimmunized mouse was determined by using an Applied Biosystems model 377 automated DNA sequencing system at Tel Aviv University Life Sciences Faculty facilities.

Double-stranded DNA templates for the-sequencing were prepared with the help of the Quiagen DNA purification kit according to manufacturer's protocol. Single-stranded DNA templates were prepared from the phage particles carrying recombinat single-chain antibodies by chloroform technique as described in Sambrook, et al.

IV Expression of scFv ME1—the single-chain antibody specific to the common epitope of mutant p53 protein—in eucaryotic cells Subcloning of the scFv ME1 gene fragment into the pIRES-EGFP, expression vector—The restriction digestion of the pIRES-EGFP was performed by incubation of the 1 µg of the vector DNA with 1 µl of 10 units/µl solution of EcoRI restriction enzyme (MEI Fermnentas, Lithuania) in EcoRI buffer at 37° C. overnight. The digested DNA was precipitated in high-salt as in (10) and de-phosphorylated by incubation with 5 µl of 1000 units/ml solution of the calf intestine alkaline phosphatase (Boehringer, Germany). The digested and de-phosphorylated DNA was purified with the help of High Pure PCR Product Purification kit (Boehringer, Germany) according to the manufacturers instructions and diluted in 100 µl of sterile distilled water.

The scFv ME1 DNA fragment was prepared by PCR amplification using the pCANTAB5E-scFvMiE1 construct as a template The reaction mix consisting of 10 µl of Taq DNA polymerase buffer, 2 µl of 10 mM dNTP solution, 8 µl of 25 mM MgC1$_2$ solution, 2 µl of 1 mM solution of the forward primer GCGAATTCATGGCCCAGGTCAA (SEQ ID NO: 6), 2 µl of 1 mM solution of the reverse primer GGAATTCAGTC-TATGCGGCACG (SEQ ID NO: 7) and 10 ng of the template DNA was diluted with sterile distilled water to total volume of 100 µl in 0.5 ml tube. The tube with reaction mixture was placed into PTC-200 thermocycler (MJ Research, USA), heated for 5 min at 95° C. and 1 µl of 5000 U/ml solution of Taq DNA polymerase (Fermentas, Lithuania) was added. The PCR reaction was run with a program as follows: 30 cycles—94° C. for 45 sec; 55° C. for 1 min; 72° C. for 30 sec. The PCR product was purified with the help of High Pure PCR Product Purification kit (Boeliringer, Germany) and 500 ng of its DNA was subjected to the restriction digestion with 1 µl of 10 units/µl solution of EcoRI restriction endonuclease (MBI Fermentas, Lithuania) in EcoRI buffer at 37° C. overnight. The digested DNA was purified as above and diluted in 50 µl of sterile distilled water.

The ligation reaction was set up by mixing 1 µl of the EcoRI—digested and de-phosphorylated pIRES-EGFP DNA solution, 6 µl of the EcoRI—digested scFv ME1 DNA solution, 2 µl of T4 DNA ligase 5×buffer, 1 µl of T4 DNA ligase (BRL ,USA) and incubated overnight at 16° C. 3 µl of the ligation mixture were taken for transformation of competent *E. coli* cells by electroporation as described in part II. Transformed cells were plated onto LB agar plates (Sambrook, et al, op. cit.) containing 100 µl of ampicillin and grown overnight at 37° C. Colonies were re-plated and their plasmid DNA was isolated using High Pure Plasmid DNA Purification kit (Boehringer, Germany). 10 µl of each plasmid DNA preparation was subjected to the restriction digestion by incubation with 0.1 µl of a solution of BamHI restriction endonuclease (Fermentas, Lithuania) at 37° C. overnight. Selected colonies were grown overnight in 10 ml of LB medium at 37° C. with shaking at 200 rpm overnight. The pIRES-EGFP-scFvME1 plasmid DNA was isolated with the help of the Qiagen Plasmid Purification kit (Quiagen, USA).

Expression of the scFv ME1 in eucaryotic cells—293 cell line (transformed primary embryonal human kidney cells) was grown in Dulbecco's Modified Eagle's Medium (DMEM) with high glucose (4.5 g/l) (Biological Industries (Israel)) supplemented with 5 mM L-glutamine (Biological Industries, Israel), 100 U/ml penicillin and streptomycin solution (Biological Industries, Israel ) and 15% heat inactivated (56° C., 30 min ) fetal calf-serum (Biological Industries, Israel). Cells were grown at 10% CO$_2$ at 37° C. in a six-well or 35 mm tissue culture plate (Costar, USA) to 50% or 70% of confluency before transfection. The transfection procedure was accomplished with the help of LipofectAMINE reagent (Gibco BRL, USA) in the following order:

1) 1.5 µg of the transfecting DNA was diluted into 100 µl of the OPTI-MEM I reduced Serum Medium (Gibco BRL, USA) in 12×75 mm sterile tubes (Falcon, USA);
2) 7 µl of LipofectAMINE reagent was diluted into 100 µl of OPTI-MEM medium in 12×75 mm sterile tubes;
3) The two solutions were combined and, mixed gently and incubated for 45 min at room temperature.
4) Following incubation, 0.8 ml of OPTI-MEM medium were added to each tube, mixed gently and overlayed onto the recipient cells pre-rinsed with 2 ml of OPTI-MEM medium.

5) After 5 hours of incubation with the transfection mixture, 1 ml of growth medium containing 30% of fetal calf-serum was added to the cells.

6) The medium was replaced with fresh, complete growth medium after 24 hours from the start of transfection.

At 48 hours after transfection cells were rinsed once with sterile PBS and EGFP fluorescence was detected by microscopy After the accomplishment of fluorescence detection, cells were harvested from tissue culure plates with the help of a "rubber policeman", resuspended in 2 ml of sterile PBS containing 0.5% of Nonidet P-40 (Sigma, USA) and incubated for 5 min on ice. The suspension was centrifuged for 5 min at 1000 rpm in a desktop centrifuge at 4° C., the supernatant containing cytosplasmic lisate was collected and frozen a 20° C. The electrophoresis and Western blot assay were performed as described in Section III.

The transfection efficiency assay was performed employing the pUT535-β gal expression vector (Cayla, France).

V. Cloning, construction and phage display of scFv from the spleen of hyperimmunized mice (a) Immunization protocol Five female BALB/c mice were immunized with the mutant p53 epitope peptide conjugated to BSA and boosted with the conjugate. To follow assay of the immunization, mice were bled and policlonal sera were prepared according to Harlow E. Lane D. (1988), op.cit. Titers of the antibodies specific to the conjugated and non-conjugated heptapeptide were measured in ELISA assay as described in Section I above.

B. EXAMPLES

1. Isolation of the single chain antibody ME1 from a phage display library prepared with the mutant p53 peptide BALB/c mice were immunized with the mutant p53 epitope peptide (FRHSVV) conjugated to BSA and boosted with the conjugate. An immunized mouse that showed the highest endpoint serum titer of antibody against the conjugate (more, than 1/1000 as tested by ELISA) was selected, its spleen removed and the spleenocites extracted by repeated washings with DMEM medium. mRNA was isolated and the spleenocites converted to cDNA by the RT-PCR procedure. Two PCR cloning reactions for the variable regions of heavy ($V_H$)- and light ($V_L$)-chains of antibody genes were performed with the primers sets in the Recombinant Antibody Phage System Kit (Pharmacia). The two DNA fragments were assembled with the linker DNA fragment from the same kit. The resulting single chain antibody (scFv) DNA was cloned into the pCANTAB 5E expression vector (Pharmacia). E. coli TG1 cells were transformed with the above construct. Phage displayed scFv molecules were produced by rescue of the phagemid pCANTAB 5E-scFv DNA with the helper phage M13KO7 from the pooled ampicillin-resistant transformants.

The biopanning was divided into two parts. In the first part, four rounds of panning were performed on ELISA plates coated with the conjugate; during the last two rounds the concentration of the conjugate on the plate was decreased sequentially by one order of magnitude per round to select the phage with the highest affinity to the peptide. As a negative control, panning on ELISA plates coated with BSA was performed. The number of phages that eluted after the fourth round of panning from the antigen-coated plates was enriched by two orders of magnitude, as compared to the BSA-coated plate. In the second part of the panning procedure, two additional rounds were carried out on ELISA plates coated with the mutant p53 protein. As before, the concentration of the antigen on the plate was decreased sequentially by one order of magnitude per round. The number of phages that eluted after the last round of panning was $10^5$ PFU.

E. Coli TG1 cells were infected with the eluted phages and their titer assayed. Single colonies obtained were used to rescue 90 individual phage clones. These were analyzed by ELISA (FIG. 1a). Six ELISA-positive phages were selected. Their specificity with respect to the antigen was analyzed in a competitive ELISA assay employing $p^53$ and the epitope peptide (FIG. 1b). Additionally, their ability to be synthesized as soluble protein separate from the phage antibody was determined. Two of the phages that produced the best yields were selected for further study.

The DNA region providing the scFv ME1 antibody gene was sequenced and is shown in FIG. 2a. The scFv coded for by this sequence was designated as ME1 (for mutant epitope). E. coli HB215 1, a non-suppressor strain, was infected with the isolated recombinant phage and soluble scFv protein was detected in the periplasmic fraction by Western blot with an antibody specific to the C-terminal epitope (E) tag of the scFv (FIG. 3).

FIG. 2a also indicates novel CDR sequences of the scFv ME1. The definitions of the CDR's were made according to Wu, T. T., & Kabat, E.A. (1970). An analysis of the sequences of the variable regions of Bence Jones proteins and myeloma light chains and their implications for antibody complementarity. J. Exp. Med. 132, 211-250). As can be seen from the figure, the CDR amino acid sequences are:

For the heavy chain:

CDR H1—YTFTSYWMN (amino acid residues H31-H35) (SEQ ID NO: 9);

CDR H2—YINPTTGYTKYNQKFKD (amino acid residues H50-H65) (SEQ ID NO: 10);

CDR-H3—GYSYFDY (amino acid, residues H95-H 102) (SEQ ID NO: 11).

For the light chain:

CDR L1—SASSSVNYMH (amino acid residues L24-L34) (SEQ ID NO: 12);

CDR L2—STSNLAS (amino acid residues L50-L56) (SEQ ID NO: 13);

CDR L3—QQRSSYPYT (amino acid residues L89-L97) (SEQ ID NO: 14).

The corresponding DNA sequences are:

For the heavy chain:

CDR H1—TACACCTTTACTAGCTACTGGATGAAC (SEQ ID NO: 15)

CDR H2—TACATTAATCCTACCACTGGTTATAC-TAAGTACAATCAG AAGTTCAAGGAC (SEQ ID NO: 16);

CDR H3—GGTTACTCTTATTTTGACTAC (SEQ ID NO:17).

For, the light chain

CDR L1—AGTGCCAGCTCAAGTGTAAATTACATG-CAC (SEQ ID NO: 18);

CDR L2—AGCACATCCAACCTGGCTTCT (SEQ ID NO: 19);

CDR L3—CAGCAAAGGAGTAGTTACCCATACACG (SEQ ID NO:20).

Also contemplated by the invention are amino acid sequences and DNA sequences having at least a 90% and 95% sequence identity to said sequence, respectively.

2. Intracellular expression of the ME1 scFv gene in the cytoplasm of mammalian cells p53 protein and its mutant forms are predomoninantly expressed in the cell cytoplasm. To check the binding activity of the ME1 scFv antibody in vivo, a cytosolic mode of ME1 scFv expression was developed. Several modifications were made in the scFv construction for expression of the scFv ME1 gene. The leader sequence required for bacterial secretion was removed and a methionine ATG start codon inserted by PCR into the ME1 scFv coding sequence. Generally, the antibody $V_H$ polypeptide starts with a glutamine residue. The immediate to vicinity of the bulky glutamine can impede successful post-translational removal of the first methionine. To cope with this situation, an alanine codon was added by PCR as a spacer after the start codon. FIG. 2b shows the sequence of scFv ME1 gene-modified for eukaryotic expression.

Following several trials, the expression vector pIRES-EGFP was chosen as the tool for intracytosolic delivery of the ME1 scFv into mammalian cells (FIG. 4). This vector employs the human cytomegalovirus major immediate early Be promoter/enhancer (CMV IE) to drive the transcription of bicistronic mRNA. Ribosomes can enter the bicistronic mRNA at the 5' end to translate the gene of interest and at the internal ribosome entry site (IRES) to translate the enhanced green fluorescent protein (EGFP) gene. pIRES-EGFP utilizes a partially disabled IRES sequence leading to a reduced rate of translation initiation at the EGFP start codon relative to that of the cloned gene. This enables detection of cells in which the mRNA, and hence the target protein, is produced at high levels to compensate for a suboptimal rate of translation of EGFP. Modified as described above, the ME1 scFv DNA sequence was inserted into the multiple cloning site (MCS) of pIRES-EGFP.

A transient expression assay was set up employing a range of host cell lines: p53 null mouse fibroblasts, the same cells stably transfected with the mutant p53 gene, and human embryonic kidney cell line 293. With the help of the β-gal reporter system, the lipofectamine transfection method was found to be optimal technique for gene delivery into the host cell lines. Upon transfection with the pIRES-EGFP-ME1 DNA construct, readily detectable amounts of EGFP fluorescence were found in 293 cells, implying a significant transcription of the, ME1 scFv gene (FIG. 5).

The invention claimed is:

1. An isolated single chain antibody capable of binding mutant p53, said smile chain antibody comprising -CDR amino acid sequences as set forth in:
   YTFTSYWMN (CDR H1 SEQ ID NO: 9);
   YINPTTGYTKYNQKFKD (CDR H2, SEQ ID NO: 10);
   GYSYFDY (CDR H3 SEQ ID NO: 11);
   SASSSVNYMH (CDR L1 SEQ ID NO: 12);
   STSNLAS (CDR L2 SEQ ID NO: 13); and
   QQRSSYPYT (CDR L3 SEQ ID NO: 14).

2. A pharmaceutical composition comprising said single chain antibody of claim 1 and a pharmaceutically acceptable excipient.

* * * * *

UNITED STATES PATENT AND TRADEMARK OFFICE
CERTIFICATE OF CORRECTION

| | |
|---|---|
| PATENT NO. | : 7,288,637 B2 |
| APPLICATION NO. | : 10/247488 |
| DATED | : October 30, 2007 |
| INVENTOR(S) | : Solomon et al. |

It is certified that error appears in the above-identified patent and that said Letters Patent is hereby corrected as shown below:

In Claim 1, at Column 23, at line 23, the word "smile" should be replaced by the word --single--.

Signed and Sealed this

Twentieth Day of May, 2008

JON W. DUDAS
*Director of the United States Patent and Trademark Office*

SEQUENCE LISTING

<160> NUMBER OF SEQ ID NOS: 8

<210> SEQ ID NO 1
<211> LENGTH: 771
<212> TYPE: DNA
<213> ORGANISM: Humanus

<400> SEQUENCE: 1

```
caggtcaaac tgcagcagtc tggggctgaa ctggcaaaac ctggggcctc agtgaagatg      60
tcctgcaaga cttctggcta cacctttact agctactgga tgaactgggt aaaacagagg     120
cctggacagg gtctggaatg gattggatac attaatccta ccactggtta tactaagtac     180
aatcagaagt tcaaggacaa ggccacattg actgcagaca aatcctccag cacggcctac     240
atgcaactga gcagcctgac caatgtggac tctgcagtct attattgtac aactggttac     300
tcttattttg actactgggg ccaagggacc acggtcaccg tctcctcagg tggaggcggt     360
tcaggcggag gtggctctgg cggtggcgga tcggacatcg agctcactca gtctccagca     420
atcatgtctg catctccagg ggagaaggtc accataacct gcagtgccag ctcaagtgta     480
aattacatgc actggttcca gcagaagcca ggcacttctc ccaaactctg gatttctagc     540
acatccaacc tggcttctgg agtccctgct cgcttcagtg gcagtggatc tgggacctct     600
tactctctca caatcagccg gatggaggct gaagatgctg ccacttatta ctgccagcaa     660
aggagtagtt acccatacac gttcggaggg ggcaccaagc tgcaaatcaa acgggcggcc     720
gcaggtgcgc cggtgccgta tccggatccg ctggaaccgc gtgccgcata g              771
```

<210> SEQ ID NO 2
<211> LENGTH: 256
<212> TYPE: PRT
<213> ORGANISM: Humanus

<400> SEQUENCE: 2

```
Gln Val Lys Leu Gln Gln Ser Gly Ala Glu Leu Ala Lys Pro Gly Ala
 1               5                  10                  15
```

-continued

```
         Ser Val Lys Met Ser Cys Lys Thr Ser Gly Tyr Thr Phe Thr Ser Tyr
                      20                  25                  30
         Trp Met Asn Trp Val Lys Gln Arg Pro Gly Gln Gly Leu Glu Trp Ile
                          35                  40                  45
         Gly Tyr Ile Asn Pro Thr Thr Gly Tyr Thr Lys Tyr Asn Gln Lys Phe
                      50                  55                  60
         Lys Asp Lys Ala Thr Leu Thr Ala Asp Lys Ser Ser Thr Ala Tyr
          65                  70                  75                  80
         Met Gln Leu Ser Ser Leu Thr Asn Val Asp Ser Ala Val Tyr Tyr Cys
                          85                  90                  95
         Thr Thr Gly Tyr Ser Tyr Phe Asp Tyr Trp Gly Gln Gly Thr Thr Val
                         100                 105                 110
         Thr Val Ser Ser Gly Gly Gly Ser Gly Gly Gly Ser Gly Gly
                     115                 120                 125
         Gly Gly Ser Asp Ile Glu Leu Thr Gln Ser Pro Ala Ile Met Ser Ala
                     130                 135                 140
         Ser Pro Gly Glu Lys Val Thr Ile Thr Cys Ser Ala Ser Ser Val
         145                 150                 155                 160
         Asn Tyr Met His Trp Phe Gln Gln Lys Pro Gly Thr Ser Pro Lys Leu
                         165                 170                 175
         Trp Ile Ser Ser Thr Ser Asn Leu Ala Ser Gly Val Pro Ala Arg Phe
                     180                 185                 190
         Ser Gly Ser Gly Ser Gly Thr Ser Tyr Ser Leu Thr Ile Ser Arg Met
                     195                 200                 205
         Glu Ala Glu Asp Ala Ala Thr Tyr Tyr Cys Gln Gln Arg Ser Ser Tyr
                     210                 215                 220
         Pro Tyr Thr Phe Gly Gly Gly Thr Lys Leu Gln Ile Lys Arg Ala Ala
         225                 230                 235                 240
         Ala Gly Ala Pro Val Pro Tyr Pro Asp Pro Leu Glu Pro Arg Ala Ala
                         245                 250                 255

<210> SEQ ID NO 3
<211> LENGTH: 780
<212> TYPE: DNA
<213> ORGANISM: Humanus

<400> SEQUENCE: 3
atggcccagg tcaaactgca gcagtctggg gctgaactgg caaaacctgg ggcctcagtg      60
aagatgtcct gcaagacttc tggctacacc tttactagct actggatgaa ctgggtaaaa     120
cagaggcctg gacagggtct ggaatggatt ggatacatta atcctaccac tggttatact     180
aagtacaatc agaagttcaa ggacaaggcc acattgactg cagacaaatc ctccagcacg     240
gcctacatgc aactgagcag cctgaccaat gtggactctg cagtctatta ttgtacaact     300
ggttactctt attttgacta ctggggccaa gggaccacgg tcaccgtctc ctcaggtgga     360
ggcggttcag gcggaggtgg ctctggcggt ggcggatcgg acatcgagct cactcagtct     420
ccagcaatca tgtctgcatc tccaggggag aaggtcacca taacctgcag tgccagctca     480
agtgtaaatt acatgcactg gttccagcag aagccaggca cttctcccaa actctggatt     540
tctagcacat ccaacctggc ttctggagtc cctgctcgct tcagtggcag tggatctggg     600
acctcttact ctctcacaat cagccggatg gaggctgaag atgctgccac ttattactgc     660
cagcaaagga gtagttaccc atacacgttc ggaggggggca ccaagctcga aatcaaacgg     720
gcggccgcag gtgcgccggt gccgtatccg gatccgctgg aaccgcgtgc cgcatagact     780
```

<210> SEQ ID NO 4
<211> LENGTH: 258
<212> TYPE: PRT
<213> ORGANISM: Humanus

<400> SEQUENCE: 4

```
Met Ala Gln Val Lys Leu Gln Gln Ser Gly Ala Glu Leu Ala Lys Pro
 1               5                  10                  15
Gly Ala Ser Val Lys Met Ser Cys Lys Thr Ser Gly Tyr Thr Phe Thr
             20                  25                  30
Ser Tyr Trp Met Asn Trp Val Lys Gln Arg Pro Gly Gln Gly Leu Glu
         35                  40                  45
Trp Ile Gly Tyr Ile Asn Pro Thr Thr Gly Tyr Thr Lys Tyr Asn Gln
 50                  55                  60
Lys Phe Lys Asp Lys Ala Thr Leu Thr Ala Asp Lys Ser Ser Ser Thr
 65                  70                  75                  80
Ala Tyr Met Gln Leu Ser Ser Leu Thr Asn Val Asp Ser Ala Val Tyr
                 85                  90                  95
Tyr Cys Thr Thr Gly Tyr Ser Tyr Phe Asp Tyr Trp Gly Gln Gly Thr
            100                 105                 110
Thr Val Thr Val Ser Ser Gly Gly Gly Ser Gly Gly Gly Gly Ser
        115                 120                 125
Gly Gly Gly Gly Ser Asp Ile Glu Leu Thr Gln Ser Pro Ala Ile Met
130                 135                 140
Ser Ala Ser Pro Gly Glu Lys Val Thr Ile Thr Cys Ser Ala Ser Ser
145                 150                 155                 160
Ser Val Asn Tyr Met His Trp Phe Gln Gln Lys Pro Gly Thr Ser Pro
                165                 170                 175
Lys Leu Trp Ile Ser Ser Thr Ser Asn Leu Ala Ser Gly Val Pro Ala
            180                 185                 190
Arg Phe Ser Gly Ser Gly Ser Gly Thr Ser Tyr Ser Leu Thr Ile Ser
        195                 200                 205
Arg Met Glu Ala Glu Asp Ala Ala Thr Tyr Tyr Cys Gln Gln Arg Ser
    210                 215                 220
Ser Tyr Pro Tyr Thr Phe Gly Gly Gly Thr Lys Leu Gln Ile Lys Arg
225                 230                 235                 240
Ala Ala Ala Gly Ala Pro Val Pro Tyr Pro Asp Pro Leu Glu Pro Arg
                245                 250                 255
Ala Ala
```

<210> SEQ ID NO 5
<211> LENGTH: 7
<212> TYPE: PRT
<213> ORGANISM: Humanus

<400> SEQUENCE: 5

```
Lys Phe Arg His Ser Val Val
 1               5
```

<210> SEQ ID NO 6
<211> LENGTH: 22
<212> TYPE: DNA
<213> ORGANISM: Humanus

<400> SEQUENCE: 6
gcgaattcat ggcccaggtc aa    22

```
<210> SEQ ID NO 7
<211> LENGTH: 22
<212> TYPE: DNA
<213> ORGANISM: Humanus

<400> SEQUENCE: 7
ggaattcagt ctatgcggca cg                                                 22

<210> SEQ ID NO 8
<211> LENGTH: 6
<212> TYPE: PRT
<213> ORGANISM: Humanus

<400> SEQUENCE: 8

Phe Arg His Ser Val Val
 1               5
```